(12) United States Patent
Cottrell et al.

(10) Patent No.: US 7,968,619 B2
(45) Date of Patent: Jun. 28, 2011

(54) COMPOSITION FOR POLYESTER FABRIC TREATMENT

(75) Inventors: Stephanie Nussbaum Cottrell, Denver, NC (US); Tirthankar Ghosh, Oreland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/713,751

(22) Filed: Feb. 26, 2010

(65) Prior Publication Data
US 2010/0234519 A1  Sep. 16, 2010

Related U.S. Application Data

(60) Provisional application No. 61/209,806, filed on Mar. 11, 2009.

(51) Int. Cl.
*C08G 79/00* (2006.01)
*C08L 85/00* (2006.01)
*C09D 5/16* (2006.01)
*D06M 13/224* (2006.01)

(52) U.S. Cl. ........ 523/122; 523/222; 252/8.81; 525/389

(58) Field of Classification Search ............... 523/122, 523/222; 252/8.81; 525/389
See application file for complete search history.

(56) References Cited

U.S. PATENT DOCUMENTS

| | | |
|---|---|---|
| 4,996,052 A | 2/1991 | McIntosh |
| 6,469,097 B1 | 10/2002 | Bett et al. |
| 2005/0226914 A1 | 10/2005 | Cottrell et al. |
| 2005/0227895 A1 | 10/2005 | Ghosh et al. |
| 2008/0115291 A1 | 5/2008 | Cottrell et al. |

FOREIGN PATENT DOCUMENTS

WO  2005080481  9/2005

*Primary Examiner* — Kriellion A Sanders
(74) *Attorney, Agent, or Firm* — Kenneth Crimaldi

(57) ABSTRACT

A composition useful for treating fabrics. The composition contains a silver-containing copolymer having polymerized units of a monomer X and a monomer Y; wherein monomer X is an ethylenically unsaturated compound having a substituent group selected from an unsaturated or aromatic heterocyclic group having at least one nitrogen atom; wherein monomer Y is selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof.

7 Claims, No Drawings

COMPOSITION FOR POLYESTER FABRIC TREATMENT

This application claims the benefit of priority under 35 U.S.C. §119(e) of U.S. Provisional Patent Application No. 61/209,806 filed on Mar. 11, 2009.

The present invention relates to a composition useful for treating polyester fabric. The composition contains a silver-polymer complex which is introduced into polyester a fabric with a polyester polyurethane and an epoxy resin to provide a treated fabric.

Use of a silver-polymer complex in combination with any epoxy resin for fabric treatment is disclosed in U.S. Pub. No. 2008/0115291. However, alternative methods for introducing silver into fabrics with good retention after washing are needed.

The problem addressed by this invention is to provide a composition that introduces a biocidal silver material to a fabric to provide a treated fabric resistant to removal of biocide by laundering.

The present invention is directed to a composition useful for treating polyester fabric. The composition comprises: (a) a silver-containing copolymer comprising polymerized units of a monomer X and a monomer Y; wherein monomer X is an ethylenically unsaturated compound having a substituent group selected from an unsaturated or aromatic heterocyclic group having at least one nitrogen atom; and wherein monomer Y is an ethylenically unsaturated compound selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof; (b) an epoxy resin; and (c) a polyester polyurethane. The invention is further directed to a method for treating polyester fabric by contacting the fabric with the composition.

The term "copolymer" as used herein and in the appended claims refers to polymers polymerized from at least two different monomers. All percentages herein are by weight, unless specified otherwise. Percentages of monomers are based on total copolymer weight.

The term "aqueous" as used herein and in the appended claims means water and mixtures composed substantially of water and water miscible solvents. The term "polyester fabric" refers to a fabric comprising at least 40% polyester, alternatively at least 50% polyester, alternatively at least 60%, alternatively at least 70%, alternatively at least 80%, alternatively at least 90%.

The use of the term "(meth)" followed by another term such as acrylic, acrylate, acrylamide, etc., as used herein and in the appended claims, refers to, for example, both acrylic and methacrylic; acrylate and methacrylate; acrylamide and methacrylamide; etc.

The glass transition temperature ("Tg") for the copolymers of the present invention may be measured by differential scanning calorimetry (DSC) taking the mid-point in the heat flow versus temperature transition as the Tg value.

In some embodiments of the present invention, the copolymer comprises at least 15 wt % of monomer X derived units. In some aspects of these embodiments, the copolymer comprises at least 20 wt % of monomer X derived units. In some aspects of these embodiments, the copolymer comprises at least 25 wt % of monomer X derived units. In some aspects of these embodiments, the copolymer comprises at least 30 wt % of monomer X derived units. In some aspects of these embodiments, the copolymer comprises at least 35 wt % of monomer X derived units, alternatively at least 40 wt %. In some aspects of these embodiments, the copolymer comprises no more than 60 wt % of monomer X derived units, alternatively no more than 55 wt %, alternatively no more than 50 wt %.

In some embodiments of the present invention, monomer X is selected from vinylimidazoles, vinylimidazolines, vinylpyridines, vinylpyrroles, derivatives thereof and combinations thereof. In some aspects of these embodiments, monomer X is selected from vinylimidazoles, vinylpyridines, derivatives thereof and combinations thereof. In some aspects of these embodiments, monomer X is selected from N-vinylimidazole, 2-vinylpyridine, 4-vinylpyridine and combinations thereof. In some aspects of these embodiments, monomer X is N-vinylimidazole (VI).

In some embodiments of the present invention, monomer Y is selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof. In some aspects of these embodiments, monomer Y is selected from carboxylic acids, carboxylic acid esters (e.g., alkyl (meth) acrylates), (meth)acrylamides, $C_8$-$C_{20}$ aromatic monomers containing at least one exocyclic ethylenic unsaturation and combinations thereof. In some aspects of these embodiments, monomer Y is selected from acrylic acid (AA), methacrylic acid, itaconic acid, maleic acid, fumaric acid, methyl (meth) acrylate, ethyl (meth)acrylate, propyl (meth)acrylate, isopropyl acrylate, n-butyl (meth)acrylate, isobutyl (meth)acrylate, 2-ethylhexyl (meth)acrylate, decyl (meth)acrylate, lauryl (meth)acrylate, stearyl (meth)acrylate, styrene, vinyltoluene, α-methylstyrene and combinations thereof. In some aspects of these embodiments, monomer Y comprises at least one $C_2$-$C_8$ alkyl (meth)acrylate, alternatively at least one $C_2$-$C_6$ alkyl (meth)acrylate, alternatively n-butyl (meth)acrylate; alternatively Y comprises at least one $C_2$-$C_8$ alkyl (meth)acrylate and at least one carboxylic acid, alternatively at least one $C_2$-$C_6$ alkyl (meth)acrylate and at least one carboxylic acid, alternatively n-butyl (meth)acrylate and at least one carboxylic acid; alternatively Y comprises at least one $C_2$-$C_8$ alkyl (meth)acrylate and (meth)acrylic acid, alternatively at least one $C_2$-$C_6$ alkyl (meth)acrylate and (meth)acrylic acid, alternatively n-butyl (meth)acrylate and (meth)acrylic acid; alternatively monomer Y comprises n-butyl acrylate (BA) and acrylic acid.

In some embodiments of the present invention, the method uses a copolymer comprising polymerized units of a monomer X and a monomer Y; wherein the copolymer comprises at least 15 wt % of monomer X derived units; wherein monomer X is selected from vinylimidazoles, vinylimidazolines, vinylpyridines, vinylpyrroles, derivatives thereof and combinations thereof; and wherein monomer Y is selected from carboxylic acids, carboxylic acid salts, carboxylic acid esters, organosulfuric acids, organosulfuric acid salts, sulfonic acids, sulfonic acid salts, phosphonic acids, phosphonic acid salts, vinyl esters, (meth)acrylamides, $C_8$-$C_{20}$ aromatic monomers containing at least one exocyclic ethylenic unsaturation and combinations thereof. In some aspects of these embodiments, the copolymer comprises no more than 5 wt % of units derived from ethylenically unsaturated monomer containing an epoxide function. In some aspects of these embodiments, the copolymer comprises no more than 1 wt % of units derived from ethylenically unsaturated monomer containing an epoxide function. In some aspects of these embodiments, the copolymer comprises no more than 0.5 wt % of units derived from ethylenically unsaturated monomer containing an epoxide function. In some aspects of these embodiments, the copolymer comprises no more than 0.1 wt % of units derived from ethylenically unsaturated monomer containing an epoxide function. In some aspects of these embodiments, the copolymer comprises no more than 0.05 wt % of units derived from ethylenically unsaturated monomer containing an epoxide function.

In some embodiments of the present invention, the composition comprising a copolymer has a pH of at least 8, alternatively at least 8.5, alternatively at least 9. In some aspects of these embodiments, the composition has a pH no greater than 10.5, alternatively no greater than 10. In some aspects of these embodiments, the composition has a pH of 8.5-10.5. In some aspects of these embodiments, the composition has a pH of 9-10.

In some embodiments of the present invention, the composition comprises a latex copolymer which has at least 20 wt % solids. In some aspects of these embodiments, the latex copolymer comprises at least 25 wt % solids. In some aspects of these embodiments, the latex copolymer comprises at least 30 wt % solids.

In some embodiments of the present invention, the composition comprises from 35 to 55 wt % of polymerized units derived from monomer X and 35 to 55 wt % of polymerized units derived from monomer Y. In some aspects of these embodiments, the composition comprises from 40 to 50 wt % of polymerized units derived from monomer X and 40 to 50 wt % of polymerized units derived from monomer Y.

In some embodiments of the present invention, the composition comprises polymerized units derived from a crosslinker. Crosslinkers suitable for use with the present invention include multi-ethylenically unsaturated monomers. In some aspects of these embodiments, the crosslinker derived units are derived from crosslinker selected from 1,4-butanediol diacrylate; 1,4-butanediol dimethacrylate; 1,6-hexanediol diacrylate; 1,1,1-trimethylol propane triacrylate; 1,1,1-trimethylol propane trimethacrylate; allyl methacrylate; divinylbenzene; and N-allyl acrylamide. In some aspects of these embodiments, the crosslinker derived units are derived from crosslinker selected from 1,1,1-trimethylol propane trimethacrylate. In some aspects of these embodiments, the composition comprises 0.01 to 10 wt % (based on solids) crosslinker. In some aspects of these embodiments, the composition comprises 0.01 to 5 wt % (based on solids) crosslinker. In some aspects of these embodiments, the composition comprises 0.01 to 1 wt % (based on solids) crosslinker.

In some embodiments of the invention, the copolymer comprises from 1 wt % to 50 wt % silver, based on total copolymer weight including silver, alternatively from 2 wt % to 40 wt %, alternatively from 3 wt % to 20 wt %, alternatively from 5 wt % to 15 wt %. Silver is in the form of Ag(I) ion, which typically is introduced in the form of silver nitrate. Methods for preparation of the copolymer have been disclosed previously, e.g., in U.S. Pat. Appl. Pub. No. US 2005/0227895. In some embodiments of the invention, to increase retention of silver by the treated fabric, additional copolymer is added which is not complexed with silver; and/or other amine compounds or polymers may be added.

In some embodiments of the invention, the epoxy resin comprises at least a difunctional epoxy compound, i.e., a compound having at least two epoxy groups per molecule. In some aspects of these embodiments, the epoxy resin comprises bis-glycidyl ethers or esters, triglycidyl isocyanurate, 1-epoxyethyl-3,4-epoxycyclohexane, vinylcyclohexene dioxide, diglycidyl esters of dicarboxylic acids, diglycidyl ethers of diols or polyols. Suitable examples of bis- and tris-glycidyl esters and ethers include bisphenol A diglycidyl ether, diglycidyl adipate; 1,4-diglycidyl butyl ether; ethylene glycol diglycidic ether; glycidyl ethers of glycerol, erythritol, pentaerythritol, trimethylol propane and sorbitol; epoxy resorcinol ethers; and diglycidyl ethers of polyethylene glycols. In some embodiments of the invention, the epoxy resin comprises a polymer of glycidyl (meth)acrylates and/or allyl glycidyl ether. In some embodiments of the invention, the epoxy resin is present in an amount that results in a 0.1:1 to 10:1 ratio of equivalents epoxide:equivalents X monomer unit. Preferably, the ratio is at least 0.2:1, alternatively at least 0.3:1, alternatively at least 0.5:1, alternatively at least 0.8:1. Preferably, the ratio is no more than 7:1, alternatively no more than 5:1, alternatively no more than 4:1.

In some embodiments of the invention, an amine curing agent in addition to the copolymer is used. Such amine curing agents are well known in the art and are described, e.g., in WO 2005/080481. These curing agents include polyfunctional primary and secondary amines and some tertiary amines, including amine-containing polymers.

The polyester polyurethane contains polymerized residues of a polyester polyol and a diisocyanate. The diisocyanate may be an aromatic diisocyanate, e.g., toluene diisocyanate (TDI), diphenyl methane diisocyanate (MDI), p-xylylene diisocyanate, tetramethylxylene diisocyanate, isomers thereof or mixtures thereof; or an aliphatic diisocyanate, e.g., 1,6-hexamethylene diisocyanate, hydrogenated methylenediphenyl diisocyanate (HMDI), ethylene diisocyanate, isophorone diisocyanate, cyclohexane-1,4-diisocyanate, or a mixture thereof. Among the aromatic diisocyanates, MDI is preferred, especially a mixture of 4,4' and 2,4' isomers. Preferred aliphatic diisocyanates include, e.g., 1,6-hexamethylene diisocyanate, hydrogenated methylenediphenyl diisocyanate (HMDI), isophorone diisocyanate and mixtures thereof. Polyester polyols include, e.g., hydroxyl terminated products of polyhydric alcohols such as ethylene glycol, propylene glycol, diethylene glycol, neopentyl glycol, trimethylol propane, glycerol, pentaerythritol, 1,4-butanediol, 1,6-hexanediol, furan dimethanol, cyclohexane 1,6-dimethanol, diols made from dimethyl carbonate and any of the above polyhydric alcohols or mixtures thereof with polycarboxylic acids or lactones, especially dicarboxylic acids such as succinic acid, adipic acid, glutaric acid, phthalic acids and caprolactone. Preferred polyester polyols include, e.g., those formed from adipic acid and diols selected from hexanediol, ethylene glycol, 1,4-butanediol, propylene glycol and cyclohexane-1,6-dimethylol. Preferably polyhydric alcohols having more than two hydroxyl groups are present to the extent of no more than 2 wt % of the polyol, alternatively no more than 1 wt %, alternatively no more than 0.5 wt %. In some embodiments of the invention, the polyurethane has Mn from 10,000 to 100,000 and Mw from 200,000 to 2,000,000 In some embodiments of the present invention, the polyester polyurethane is an aliphatic polyester polyurethane, i.e., it contains polymerized residues of an aliphatic polyester polyol and an aliphatic diisocyanate.

Some embodiments of the present invention will now be described in detail in the following Examples. All fractions and percentages set forth below in the Examples are by weight unless otherwise specified.

General Sample Preparation Procedure: The level of silver-containing copolymer in the bath solution was maintained at 181 ppm silver to provide 300 ppm of silver on the dried fabric. The bath was made using tap water that was pH adjusted using 28% NH$_4$OH to a pH of 9.5-9.9, prior to the addition of the silver-containing copolymer. Other ingredients were added at appropriate levels—the solution was mixed using a standard air mixer until homogeneous. The substrate to be treated was passed through the bath solution and then passed through two nips rolls to express excess solution. The treated substrate is tentered and dried 2-3 min@149-163° C., The treated, dried substrate is washed as noted, and then submitted for Ag content and/or efficacy testing.

Samples were prepared with a silver-containing copolymer which had 45 wt % BA monomer units, 45 wt % VI monomer units and 10% AA monomer units, and which contained 11% silver, and/or with the epoxy resins/polyurethanes indicated in the tables below added to the treatment water. The amount of epoxy resin was measured in equivalents epoxy group/equivalent of VI unit in the silver-containing copolymer. The fabric substrate used for the testing was 100% polyester knit fabric, 3.5 oz/yd$^2$ (125 g/m$^2$) basis weight.

TABLE 1

Various Levels of Silver-Containing Copolymer vs Various Levels of Epoxy Resin Epi-Rez 3510-W-60 and Different Polyurethanes: Silver Retention Values

| Wash Cycles[1] | Ag content, ppm | % Ag Retained | Epoxy Resin (Epi-Rez 3510-W-60[2]), g/g Ag polymer | Polyurethane[3], 8.82 g/g Ag polymer, PU1:PU2:PU3 (wt.) |
|---|---|---|---|---|
| 0 | 337 | NA | 1.88 (1.5 eq/VI) | 0:1:0 |
| 2 | 210 | 62.3 | | |
| 4 | 199 | 59.1 | | |
| 10 | 76 | 22.6 | | |
| 0 | 303 | NA | 3.76 (3 eq/VI) | 1:1:0 |
| 2 | 213 | 70.3 | | |
| 4 | 161 | 53.1 | | |
| 10 | 47 | 15.5 | | |
| 0 | 321 | NA | 3.76 (3 eq/VI) | 0:0:1 |
| 2 | 233 | 72.6 | | |
| 4 | 213 | 66.4 | | |
| 10 | 103 | 32.1 | | |
| 0 | 297 | NA | 2.82 (2.25 eq/VI) | 1.25:1.0:1.08 |
| 2 | 239 | 80.5 | | |
| 4 | 199 | 67.0 | | |
| 10 | 62 | 20.8 | | |
| 0 | 285 | NA | 1.88 (1.5 eq/VI) | 1:0:1 |
| 2 | 222 | 77.9 | | |
| 4 | 164 | 57.5 | | |
| 10 | 72 | 25.3 | | |
| 0 | 295 | NA | 1.88 (1.5 eq/VI) | 0:0:1 |
| 2 | 239 | 81.0 | | |
| 4 | 195 | 66.1 | | |
| 10 | 97 | 32.9 | | |
| 0 | 323 | NA | 3.76 (3 eq/VI) | 1:0:0 |
| 2 | 195 | 62.3 | | |
| 4 | 153 | 59.1 | | |
| 10 | 45 | 22.6 | | |
| 0 | 292 | NA | 3.76 (3 eq/VI) | 0:0:1 |
| 2 | 225 | 77.1 | | |
| 4 | 189 | 64.7 | | |
| 10 | 70 | 24.0 | | |
| 0 | 283 | NA | 2.82 (2.25 eq/VI) | 1.25:1.0:1.08 |
| 2 | 232 | 82.0 | | |
| 4 | 199 | 70.3 | | |
| 10 | 84 | 29.7 | | |
| 0 | 309 | NA | 3.76 (3 eq/VI) | 0:1:1 |
| 2 | 249 | 80.4 | | |
| 4 | 220 | 71.2 | | |
| 10 | 96 | 31.1 | | |
| 0 | 290 | NA | 1.88 (1.5 eq/VI) | 1:1:1 |
| 2 | 226 | 77.9 | | |
| 4 | 172 | 59.3 | | |
| 10 | 64 | 22.1 | | |
| 0 | 310 | NA | 1.88 (1.5 eq/VI) | 1:0:0 |
| 2 | 237 | 76.5 | | |
| 4 | 172 | 55.5 | | |
| 10 | 64 | 20.6 | | |
| 0 | 291 | NA | 2.82 (2.25 eq/VI) | 1.25:1.0:1.08 |
| 2 | 267 | 89.7 | | |
| 4 | 228 | 78.4 | | |
| 10 | 111 | 38.1 | | |
| 0 | 293 | NA | 2.82 (2.25 eq/VI) | 1.25:1.0:1.08 |
| 2 | 258 | 88.1 | | |
| 4 | 200 | 68.1 | | |
| 10 | 62 | 21.2 | | |
| 0 | 315 | NA | 3.76 (3 eq/VI) | 1:0:1 |
| 2 | 238 | 74.6 | | |
| 4 | 179 | 56.8 | | |
| 10 | 80 | 25.4 | | |
| 0 | 307 | NA | 1.88 (1.5 eq/VI) | 1:0:0 |
| 2 | 225 | 73.3 | | |
| 4 | 183 | 59.6 | | |
| 10 | 53 | 17.3 | | |
| 0 | 274 | NA | 3.76 (3 eq/VI) | 1:0:1 |
| 2 | 201 | 73.4 | | |
| 4 | 163 | 59.5 | | |
| 10 | 43 | 15.7 | | |
| 0 | 285 | NA | 1.88 (1.5 eq/VI) | 1:1:1 |
| 2 | 189 | 66.3 | | |
| 4 | 113 | 39.6 | | |
| 10 | 29 | 10.2 | | |
| 0 | 275 | NA | 3.76 (3 eq/VI) | 1:1:1 |
| 2 | 187 | 68.0 | | |
| 4 | 128 | 46.5 | | |
| 10 | 37 | 13.5 | | |
| 0 | 276 | NA | 3.76 (3 eq/VI) | 1:0:0 |
| 2 | 221 | 80.0 | | |
| 4 | 111 | 40.2 | | |
| 10 | 38 | 13.8 | | |
| 0 | 286 | NA | 3.76 (3 eq/VI) | 0:1:0 |
| 2 | 175 | 61.2 | | |
| 4 | 110 | 38.5 | | |
| 10 | 27 | 9.4 | | |
| 0 | 300 | NA | 3.76 (3 eq/VI) | 0:1:0 |
| 2 | 202 | 67.3 | | |
| 4 | 119 | 39.7 | | |
| 10 | 30 | 10.0 | | |
| 0 | 323 | NA | 2.25 (2.25 eq/VI) | 1.25:1.0:1.08 |
| 2 | 201 | 62.2 | | |
| 4 | 152 | 47.1 | | |
| 10 | 27 | 8.4 | | |
| 0 | 284 | NA | 1.88 (1.5 eq/VI) | 1:1:0 |
| 2 | 185 | 65.0 | | |
| 4 | 114 | 40.1 | | |
| 10 | 22 | 7.7 | | |
| 0 | 275 | NA | 2.82 (2.25 eq/VI) | 1.25:1.0:1.08 |
| 2 | 203 | 73.8 | | |
| 4 | 128 | 46.5 | | |
| 10 | 80 | 29.1 | | |
| 0 | 280 | NA | 1.88 (1.5 eq/VI) | 0:1:1 |
| 2 | 228 | 81.4 | | |
| 4 | 176 | 62.9 | | |
| 10 | 54 | 19.3 | | |

[1]AATCC Method 61 Type 2A wash using LAUNDER-OMETER ®; 1 cycle simulates 5 home machine washings
[2]EPI-REZ ™ 3510-W-60 bisphenol A glycidyl ether dispersion ("ER 3510-W-60", 185-215 equiv. wt. per epoxide, solids basis, available from Hexion, Inc.)
[3]PU1 = SANCURE-777 (Lubrizol Corp.; aliphatic polyester polyurethane; 35% solids) PU2 = SANCURE-861 (Lubrizol Corp.; aliphatic polyester polyurethane; 40% solids) PU3 = SANCURE-2026 (Lubrizol Corp.; aliphatic polyester polyurethane; 40% solids)

TABLE 2

Various Levels of Epoxy-Containing Polymers and Different Polyurethanes: Silver Retention Values

| Wash Cycles[1] | Ag content, ppm | Epoxy Resin (g/g Ag polymer) | Polyurethane, 9.02 g/g Ag polymer |
|---|---|---|---|
| 0 | 336.5 | none | PU3 |
| 2 | 31 | | |
| 4 | 4.7 | | |
| 10 | ND | | |
| 0 | 341.3 | SR-GLG[2] | PU3 |
| 2 | 193 | 0.27 (0.5 eq/VI) | |
| 4 | 89.6 | | |
| 10 | 6.7 | | |
| 0 | 335.3 | SR-GLG[2] | PU3 |
| 2 | 288.9 | 0.82 (1.5 eg/VI) | |
| 4 | 229.4 | | |
| 10 | 71.5 | | |
| 0 | 356.8 | SR-GLG[2] | PU3 |
| 2 | 273.0 | 1.62 (3.0 eq/VI) | |
| 4 | 236 | | |
| 10 | 116.4 | | |
| 0 | 399.0 | SR-GLG[2] | none |
| 2 | 70.4 | 0.27 (0.5 eq/VI) | |
| 4 | 34.5 | | |
| 10 | 2.1 | | |
| 0 | 347.3 | SR-GLG[2] | none |
| 2 | 64.7 | 0.82 (1.5 eq/VI) | |
| 4 | 36.3 | | |
| 10 | 4.4 | | |
| 0 | 369.5 | SR-GLG[2] | none |
| 2 | 56.1 | 1.62 (3.0 eq/VI) | |
| 4 | 30.5 | | |
| 10 | 6 | | |
| 0 | 308 | SR-GLG[2] | none |
| 2 | 47 | 0.82 (1.5 eq/VI) | |
| 4 | 29 | | |
| 10 | <20 | | |
| 0 | 276 | SR-GLG[2] | PU3 |
| 2 | 157 | 0.82 (1.5 eq/VI) | |
| 4 | 144 | | |
| 10 | 62 | | |
| 0 | 286 | GE-23[3] | none |
| 2 | 22 | 1.08 (1.5 eq/VI) | |
| 4 | <20 | | |
| 10 | <20 | | |
| 0 | 263 | GE-23[3] | PU3 |
| 2 | 76 | 1.08 (1.5 eq/VI) | |
| 4 | 35 | | |
| 10 | <20 | | |
| 0 | 299 | GE-30[4] | none |
| 2 | 45 | 0.82 (1.5 eq/VI) | |
| 4 | <20 | | |
| 10 | <20 | | |
| 0 | 235 | GE-30[4] | PU3 |
| 2 | 101 | 0.82 (1.5 eq/VI) | |
| 4 | 56 | | |
| 10 | <20 | | |
| 0 | 359 | EpiRez 3510-W-60 | none |
| 2 | 62 | 1.88 (1.5 eq/VI) | |
| 10 | 7 | | |
| 0 | 340 | EpiRez 3510-W-60 | PU2 |
| 2 | 143 | 1.88 (1.5 eq/VI) | |
| 10 | 2 | | |
| 0 | 362 | none | PU2 |
| 2 | 0.4 | | |
| 10 | ND | | |
| 0 | 348 | EpiRez 3510-W-60 | PU4 |
| 2 | 49 | 1.88 (1.5 eq/VI) | |
| 10 | 1 | | |
| 0 | 350 | none | PU4 |
| 2 | ND | | |
| 10 | ND | | |

[1]AATCC Method 61 Type 2A
[2]SR-GLG (Sakamoto Yakuhin Kogyo Co.; glycerol polyglycidyl ether; epoxy eq. wt. 143)
[3]Erisys GE-23 (CVC Specialty Chemicals polypropylene glycol diglycidyl ether)
[4]Erisys GE-30 (CVC Specialty Chemicals; trimethylolpropane triglycidyl ether)
PU4 = PRIMAL U-51 (Rohm and Haas Co.; polycaprolactone polyurethane)

The invention claimed is:

1. A composition useful for treating fabric; said composition comprising:
   (a) a silver-containing copolymer comprising polymerized units of a monomer X and a monomer Y; wherein monomer X is N-vinylimidazole; wherein monomer Y comprises at least one alkyl (meth)acrylate; and wherein the copolymer comprises 5 wt % to 15 wt % silver, based on total copolymer weight;
   (b) an epoxy resin; and
   (c) an aliphatic polyester polyurethane.

2. The composition of claim 1, wherein the copolymer comprises 35 to 55 wt % of units derived from monomer X and 35 to 55 wt % of units derived from monomer Y.

3. The composition of claim 2, wherein monomer Y comprises n-butyl acrylate and acrylic acid.

4. The composition of claim 2, wherein the epoxy resin is trimethylol propane tri-glycidyl ether.

5. A method of treating fabric, said method comprising contacting the fabric with the composition of claim 1.

6. The method of claim 5, wherein the copolymer comprises 35 to 55 wt % of units derived from monomer X and 35 to 55 wt % of units derived from monomer Y.

7. The method of claim 6, wherein monomer Y comprises n-butyl acrylate and acrylic acid.

* * * * *